United States Patent [19]

Carrieri

[11] Patent Number: 5,241,179
[45] Date of Patent: Aug. 31, 1993

[54] THERMOLUMINESCENCE SENSOR FOR THE REMOTE DETECTION OF CHEMICAL AGENTS AND THEIR SIMULANTS

[75] Inventor: Arthur H. Carrieri, Abingdon, Md.

[73] Assignee: The United States of America as represented by the Secretary of the Navy, Washington, D.C.

[21] Appl. No.: 976,854

[22] Filed: Nov. 16, 1992

Related U.S. Application Data

[63] Continuation of Ser. No. 756,747, Sep. 9, 1991, abandoned.

[51] Int. Cl.⁵ .......................... G01V 5/00; G01J 1/58
[52] U.S. Cl. .................................. 250/341; 250/253; 250/338.5
[58] Field of Search .................. 250/338.5, 341, 458, 250/253, 255; 356/318

[56] References Cited

U.S. PATENT DOCUMENTS

| | | | |
|---|---|---|---|
| 4,222,744 | 9/1980 | McConnell | 356/318 X |
| 4,247,770 | 1/1981 | Welch | 250/253 |
| 4,496,839 | 1/1985 | Bernstein et al. | 250/341 |

Primary Examiner—Constantine Hannaher
Assistant Examiner—Edward J. Glick
Attorney, Agent, or Firm—Anthony T. Lane; Edward Goldberg; Michael C. Sachs

[57] ABSTRACT

A system for remotely detecting liquid contaminants on surfaces, including chemical agents and their simulants is presented. The system includes a Fourier Transform Infrared Spectroradiometer aligned to optionally develop graybody photoluminescence spectra from the generation of a plurality of interferograms co-added to provide a favorable signal to noise ratio for use with and thereafter transforming the co-added interferograms. A laser is used for surface irradiating a substrate potentially having the chemical agents to heat the substrate. A shutter controls the laser to receive and record photoluminescence emissions from the heated substrate, and generate a plurality of interferograms co-added to provide a favorable signal to noise ratio for use with the Fourier Transform Infrared Spectroradiometer. The co-added interferograms are used to generate molecular absorption resonant peaks which are mathematically processed in the Fourier Transform Infrared Spectroradiometer. The acquired data is processed to match the spectrum of known chemical agent and the measured difference emissions spectrum during irradiation. If a match exists, the presence of chemical agents is confirmed. A digital filter may be used to extract the chemical agent emission band which are distinct from the emission bands of the substrate sought by the detection system.

3 Claims, 8 Drawing Sheets

THERMOLUMINESCENCE SENSOR FOR THE REMOTE DETECTION OF CHEMICAL AGENTS AND THEIR SIMULANTS

GOVERNMENTAL INTEREST

The invention described herein may be made, used, or licensed by or for the Government for Governmental purposes without the payment to me of any royalties thereon or therefor.

This application is a continuation of application Ser. No. 07/756,747, filed Sep. 9, 1991, abandoned.

FIELD OF THE INVENTION

The present invention relates to a method and apparatus for remote detection of chemical agents, and more particularly to a method and apparatus for detecting specific liquid carcinogens and chemical agents on natural surfaces such as soil and sand without risk to unprotected personnel.

BACKGROUND OF THE INVENTION

The presence of dispersed liquid carcinogens and chemical agents on natural surfaces such as soil and sand pose considerable risk to unprotected personnel. Development and application of a standoff detection technology that can sense contaminants on/within terrestrial and manufactured surfaces through their infrared (IR) absorption/emission signatures would allow personnel to protect themselves and take the appropriate action to decontaminate, or to avoid the contaminated areas altogether. It is therefore an object of this invention to provide this capability.

When IR-absorbing liquids are dispersed on sand and soil surfaces in low quantity, their molecular absorption resonant peaks are revealed from a Fourier Transform Infrared (FTIR) spectroradiometer as the surfaces undergo external heating by a laser beam source or other suitable beam source irradiation. Furthermore, the laser dwell time of an isotopic $CO_2$ laser beam required to elevate surface temperature for target (target and contaminant are synonymous (identification is lower when the irradiating beam is polarization-modulated.

In the early 1906's, the U.S. Army Chemical Systems Laboratory (now known as the U.S. Army Chemical Research, Development, and Engineering Center or CRDEC) had started various remote sensing programs for detecting threat chemical and biological agents in vapor cloud, aerosol, rain, and surface contamination scenarios. Short-path IR point sensor and spectral filter wheel devices were the first evaluated. A need for passive spectroscopic techniques that collect and process radiance from natural or preexisting sources was identified in the early 1970's and advanced development on the U.S. Army's field remote chemical agent detection unit, denoted as the XM21 unit was underway in 1979. The technology the XM21 instrument was based on originated from the famous Michelson-Morley experiments, published in 1887. Modern active systems that provide a coherent and highly directional laser source with which to irradiate a target for identification started with Raman studies in the mid to late 1970's. (The Raman effect was first predicted in 1923 by Adolf Smekal and observed experimentally in 1928 by Chandrasekhara Vankata Raman.) In addition, research started in the early 1980's on applying laser induced fluorescence and DISC/DIAL, (Differential Scattering/Differential Absorption LIDAR—Light Detection and Ranging) technologies for remote chemical/biological detection. DISC/DIAL devices show the most promise, and are the most technologically advanced vapor detection and range resolve systems currently in operation.

While some instruments exploiting the above technologies are successful in detecting specific vapor agent clouds and their simulants in the open atmosphere at low concentration lengths and at ranges in the kilometers, a reliable technology to sense ground contaminants below mass densities proven harmful to life is not yet known to have been developed.

It is therefore still another object of the present invention to provide a system which proves a capability for detecting chemical agent simulants DMMP (Dimethyl methyl phosphonate), DIMP (Diisopropyl methyl phosphonate), or SF96 (polydimethyl Siloxane, a long chain silicon base oily liquid of low vapor pressure) applied to soil and sand surfaces, in $\sim 0.3$ ml (droplet) quantity or below.

Other objects and advantages will appear hereinafter.

SUMMARY OF THE INVENTION

It has now been discovered that the above and other objects of the present invention may be accomplished in the following manner.

The system includes a Fourier Transform Infrared Spectroradiometer aligned to optically develop dynamic photoluminescence spectra generated from a plurality of interferograms co-added to provide a favorable signal to noise ratio then fast Fourier transformed by a mathematical algorithm. An isotopic carbon dioxide ($CO_2$) laser is used to produce the photoluminescent signal from the substrate potentially having the chemical agents. A shutter controls sample beam exposure to receive and record photoluminescent emissions from the heated substrate, and generate a plurality of interferograms, which then are co-added to provide a favorable signal to noise ratio, for use with the Fourier Transform Infrared Spectroradiometer.

The co-added interferograms contain the molecular absorption resonant peaks of the contaminant, and are revealed by Fourier transformation via a mathematical algorithm integrated into the Spectroradiometer. The acquired photoluminescent emissions data are processed during a heating interval when the photoluminescent emission flux (rate of emissions liberated) is minimum. In this beam-heating interval, contiguous sets of co-added interferograms are fast Fourier transformed and subtracted to determine the presence of absorption/emission bands of the chemical agents.

In a preferred embodiment, the system includes optical means for selectively (a) directing and tracking said laser beam onto a fixed target area so that the area scanned by the beam fills the field-of-view of the detector in said Fourier Transform Infrared spectroradiometer, and (b) replacing the heating source with the more powerful non-isotopic $CO_2$ laser operating at its high-gain 10.6 $\mu$ emission line. With this embodiment, the shutter will operate intermittently so that data from the sample will be collected by said Spectroradiometer only when the beam is blocked (shutter closed), and the surface will be heated only when the beam is unobstructed (shutter open). With this embodiment, an optical filter to block scattered beam radiance from entering the interferometer is not required.

The laser adapted in said photoluminescent sensor operates at an energy strongly absorbed by said substrate and outside the particular optical bandwidth of the Fourier Transform Infrared Spectrometer where the chemical contaminants present their absorption bands.

The following table is a listing of the contaminants detected by said photoluminescent sensor, their molecular formulae, vibrational resonance bands, and vapor pressures. The labeled bands refer to sensor data illustrated in FIGS. 3a–b.

TABLE I

Liquid contaminants and some important physical properties for remote detection

| Contaminant | Label FIGS. 2, 3 | Freq. ($cm^{-1}$) | Assign. | Inten. | Vapor Pressure [$\log_{10} P(torr)$] |
|---|---|---|---|---|---|
| $CH_3PO(OCH_3)_2$ | 2c | 1049 | $\nu(C-O)$ | vs | $9.0 - \frac{2736.3}{T(°K.)}$ |
| DMMP | 2d | 1061 | $\nu(C-O)$ | vs | |
| | 2e | 1072 | $\nu(C-O)$ | s | |
| | 2g | 1273 | $\nu(P=O)$ | m | |
| $CH_3PO(OCH(CH_3)_2)_2$ | 2a | 995 | $\nu(P-O-C)$ | vs | $5.7 - \frac{878.6}{T(°K.) - 162.55}$ |
| DIMP | 2b | 1014 | $\nu(P-O-C)$ | m | |
| | 2f | 1261 | $\nu(P=O)$ | m | |
| $[Si(CH_3)_2O-]_n$ | 3a | 1034 | $\nu(Si-O-Si)$ | vs | negligible |
| $SF_{96}$ | 3b | 1092 | $\nu(Si-O-Si)$ | vs | |
| | 3c | 1265 | $\delta(Si-CH_3)$ | m | | vs: very strong; s: strong; m: medium

In another embodiment, the laser beam is to provide rapid, continuous, and periodic changes in laser beam polarization to achieve more rapid heating of said substrate and therefor less beam irradiation time for first detection of the chemical contaminant(s). This effect decreases the time to achieve thermal equilibrium on said substrate.

BRIEF DESCRIPTION OF THE DRAWINGS

For a more complete understanding of the invention, reference is hereby made to the drawings, in which:

FIG. 4b tracks the energy shift of the peak emission of FIG. 4a. FIGS. 4a–b show that the surface can be made to emit greater photoluminescent flux by modulating the polarization state of the irradiating beam.

DETAILED DESCRIPTION OF THE PREFERRED EMBODIMENTS

The laboratory experimental system used here for data collection and analysis is relatively simple, incorporating both passive and active features. Passive in distinction because the sensor utilized to process radiant energy for its spectral content was designed solely for detection of specific chemical agent clouds in the atmosphere via collected ambient radiance. The interferometer is based on a spectroradiometer built by Honeywell, Incorporated. Its active feature is the laser irradiance that pumps the photoluminescent radiance.

As has been previously stated, a detection event is accomplished provided that the contaminant possesses at last one strong infrared resonance band, that the surface is irradiated at an energy strongly absorbed by the surface, and that the scattered beam energy is prevented from entering the interferometer.

Figure 1:
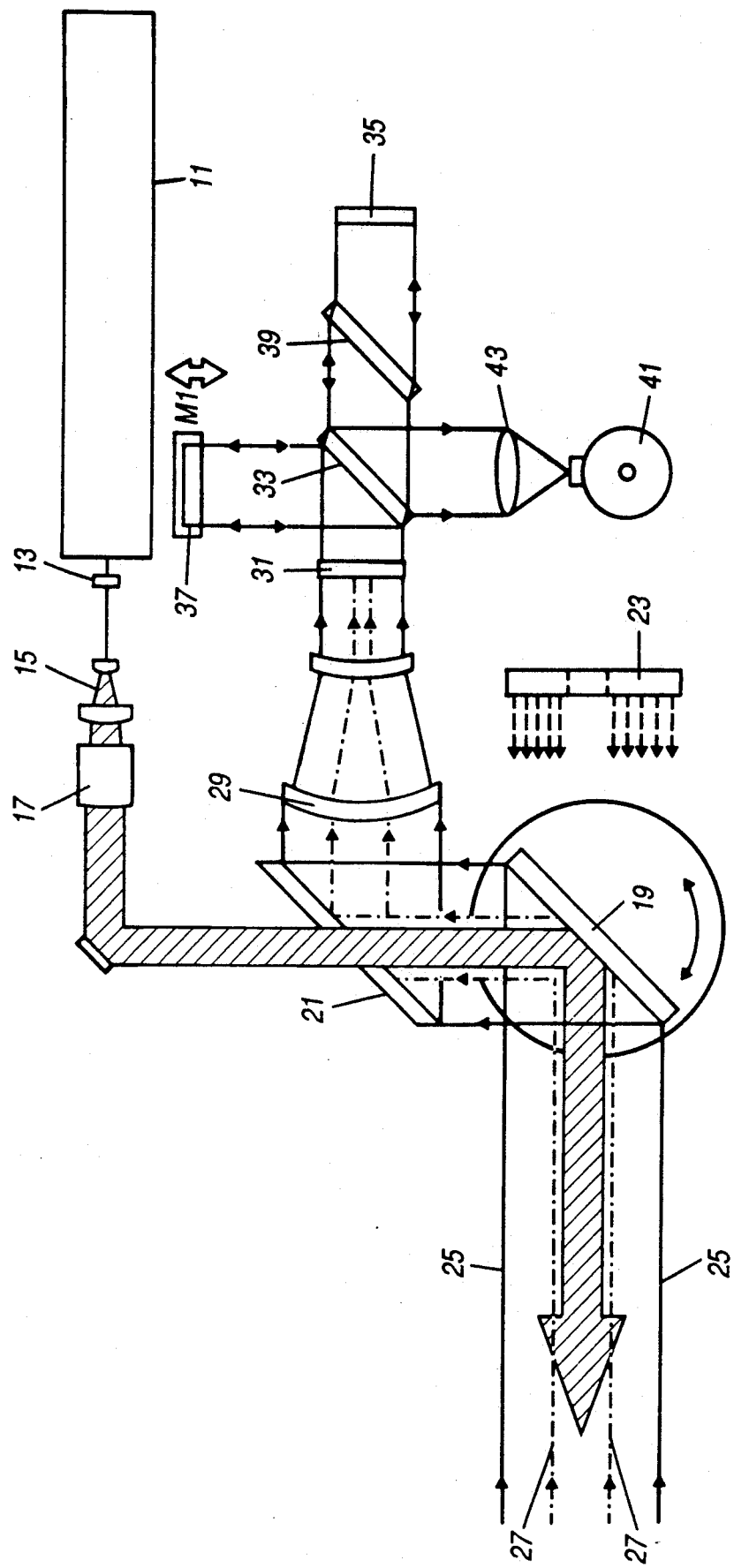
FIG. 1 is a schematic view showing the direction of the system of the present invention toward a substrate.

Laser 11 is shown in FIG. 1. It might be embodied if desired, by a sealed, continuous wave, laser containing isotopic $C^{14}O_2^{16}$ and inert gaseous mixtures as its gain medium, with its beam vertically polarized and its wavelength 12.08 $\mu m$ from the $CO_2$ P(44) transition, $00^01-10^00$ band. Shutter 13 is used to block the beam during internal calibration operations when blackbody radiance from source 23 transmits through a polystyrene plate, detected, then resolved into its characteristic absorption profile. Beam expander 15 is used to reduce the divergence of the irradiation beam, and photoelastic modulator 17 is used for rapidly altering the incident beam's polarization state.

Figure 4A:
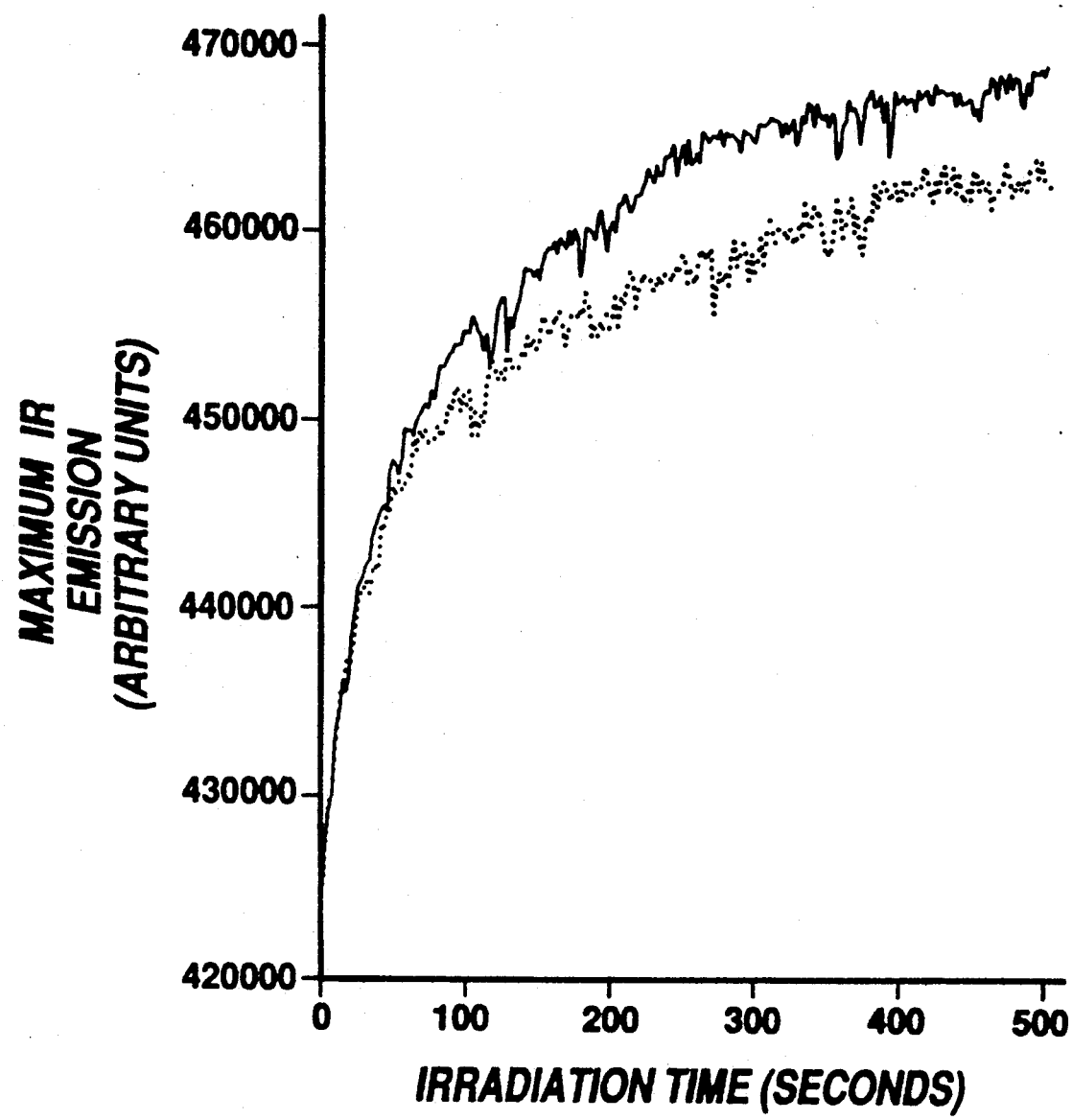
FIG. 4a is data that tracks the peak infrared emission of a sand surface during beam irradiation when the beam is fixed and modulated in polarization.
Figure 4B:
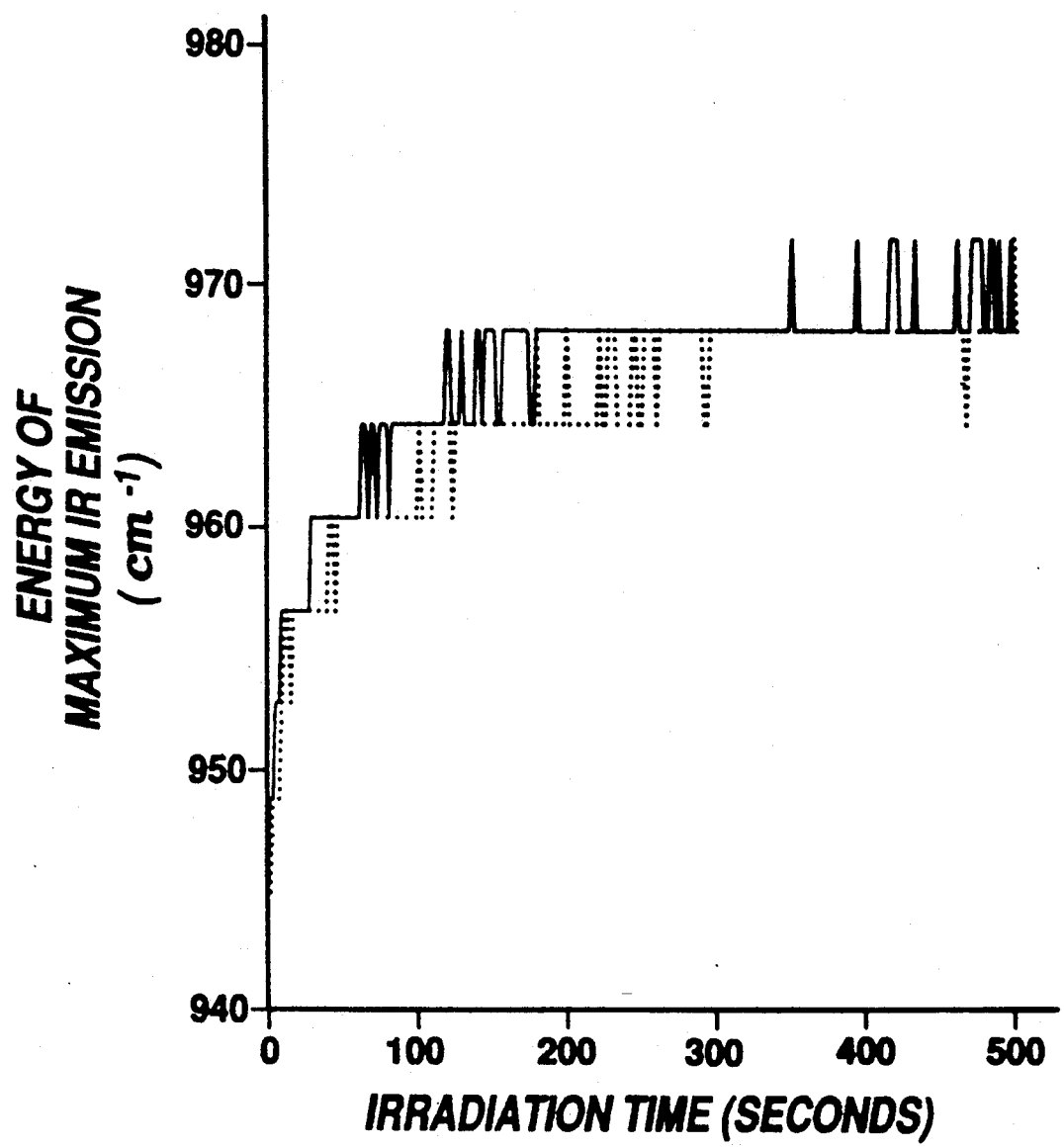

The photoelastic modulator 17 is an improvement and forms part of the preferred embodiment, but is not a required component of the detection system of this invention. It was observed that by modulating beam polarization using photoelastic modulator 17, surface temperature rises more sharply than with a fixed linearly polarized beam for the first seconds-minute of irradiation time, i.e., time required to attain thermal equilibrium. Moreover, irradiation dwell time necessary for evolving target spectra is reduced when the photoelastic modulator 17 is active. In FIGS. 4A and 4B energy levels are plotted, the broken lines are measurements when there is not polarization modulation; the solid lines are when there is polarization modulation. It takes less energy to get the same result when there is polarization modulation.

It is not clear why polarization modulation has an enhancing effect in the evolving target signature. Apparently, absorption coefficients in contaminated soil and sand surfaces tested show a slight polarization dependence.

IR mirror 19 is mounted to a rotary and scanning platform. It directs and tracks the laser beam onto a fixed target area, and reflects scattered and thermal radiant energy to mirror 21. Its other function is to reflect (shutter closed, mirror indexed into position) blackbody radiance from source 23 to mirror 21, which directs it into the interferometer. When blackbody source 23 is at ambient temperature an scanner mirror indexed into calibration position, its blackbody radiance is reflected by mirror 21 and passed through a polystyrene plate which is inserted before optical filter 31. The interferometer will subsequently measure the absorption of the known polystyrene calibrator and an onboard computer will adjust the servo-mechanism controlling oscillating mirror 37 if the measured absorption hands do not match their known values. The sample data collection mode of operation begins after calibration and the scanner mirror is indexed so that the interferometer detector 41 view the surface to be irradiated. With shutter 13 still closed, graybody radiance of the suspected contaminated surface is collected under ambient conditions. These data will establish a reference graybody spectrum of the prevailing thermal state of the suspected contaminated surface. Shutter 13 next opens and passes the beam to the surface viewed by interferometer detector 41. This data collection mode begins when emissions from the surface under irradiation shift relative to the ambient graybody spectra some predetermined amount. (The shift is proportional to temperature increase, which is independent on the power density of the irradiating beam.) Emissive light rays 25 and scattered light rays 27 are emanated from the sample and directed to the interferometer. Mirror 21 has a hole through its center at 45 degrees, wide enough to pass the outgoing beam. Beam condenser 29 collects all reflected radiant energy from mirror 21, reduces it in area, and passes the increased intensity (energy per unit area) through the limited aperture of the Fourier Transform Infrared (FTIR) spectrometer. A low-pass optical filter 31 blocks scattered light yet passes al 8 $\mu$m thermal radiance.

The remainder of the system consists of a Michelson interferometer FTIR spectroradiometer of the type referenced above. Incoming light that passes filter 31 is amplitude-divided by 50-50% beam splitter 33, at 45 degrees to the incident light. Mirror 35 is fixed in position, while mirror 37 harmonically vibrates parallel to the incident wavefront at 5 Hz, effectively changing the relative path and thus phase difference between split wavefronts.

Located just before the mirror 35 is compensating plate 39, oriented at 45 degrees and identical to beam splitter 33 except for the reflection coating. It compensates for phase changes imparted each time light traverses through beam splitter 33. It can be noted that two paths are taken by rays incident to the detector. Light rays incident to and reflected by mirror 37 traverse through beam splitter 33 three times, while light rays incident to and reflected by mirror 35 traverse through beam splitter 33 once and compensating plate 39 twice. Mirrors 37 and 35 return the split wavefronts to beam splitter 33, producing interference according to their difference in path lengths (phases). Fringes that result from interference are swept by the effects of moving mirror 37, therefore, a real time interferogram is transmitted to the liquid nitrogen cooled Mercury-Cadmium Telluride detector chip 41 via reducing/imaging lens 43. The temporal fringe pattern is converted by the detector into a variable voltage signal, digitized, and the latter processed with software (a fast Fourier transformation algorithm) to produce spectral amplitudes.

Figure 2:
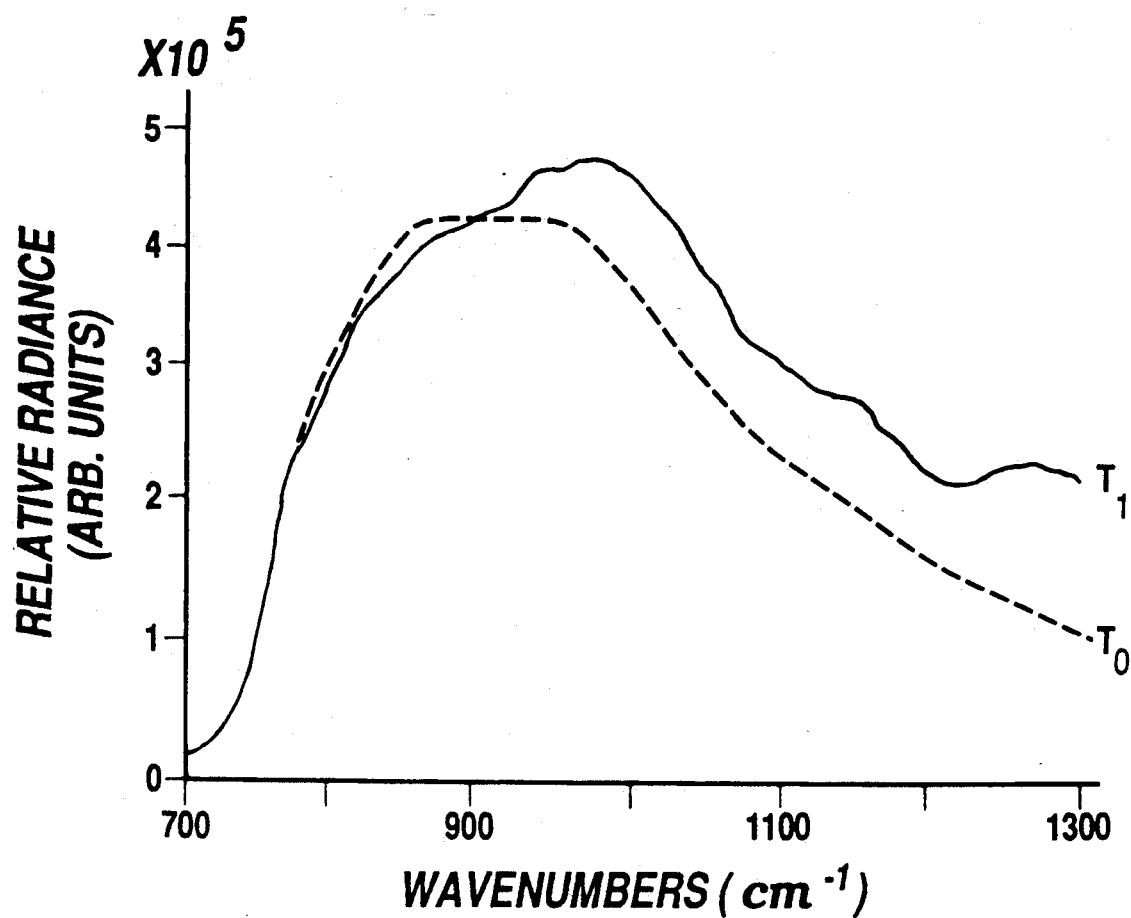
FIG. 2 is a plot of radiant energy versus frequency from data taken by use of the present invention.

In order to evaluate the system shown in FIG. 1, various experiments were performed. The distance between a sample and the entrance aperture of the interferometer was about one meter in the tests shown in FIG. 2 as well as in all other measurements reported here. Plotted in FIG. 2 are relative radiance (amplitude of the Fourier spectrum) in arbitrary units versus wave numbers (reciprocal wavelengths) in inverse centimeters from a sand surface under two conditions: (a) ambience or $T_0$, the laser is off and room temperature of the soil is $T_0 = 23.3$ degrees C.; and (b) when the laser irradiates for almost 10 minutes, causing a spectral shift in the sand's 8-12 $\mu$m thermal emission envelope, as generated by a 0.61 Watt/cm$^2$ intense beam. For this particular data the photoelastic modulator 17 is not active as the incident laser beam is fixed linear-vertical in polarization. According to calibration data from a variable-temperature blackbody source, a 75 cm$^{-1}$ frequency shift correlates to a $\Delta T = T - T_{ambient}$ 32 33 degrees Centigrade (C.) surface temperature rise. This is determined by calibration of spectrum shifts in a known variable temperature blackbody source with shifts produced in the laser/FTIR data. It can be noticed in FIG. 2 that the radiant energy shift is less apparent on the low frequency end because optical filter 31 blocks most energy at 826 cm$^{-1}$ and below, thus the sharp roll-off.

Two emission Restrahlen bands in sand between 1100-1300 cm$^{-1}$ have emerged in the elevated temperature $T_1$ spectrum. Provided that high enough temperatures are generated on and within contaminated surfaces, spectral information on both surface and contaminant evolve and are separable in the Fourier transformed difference spectra. Distinct absorption and emission bands of liquid agent stimulants were repeatably observed and are distinguished from the broader sand and soil emission background spectra.

Figure 3A:
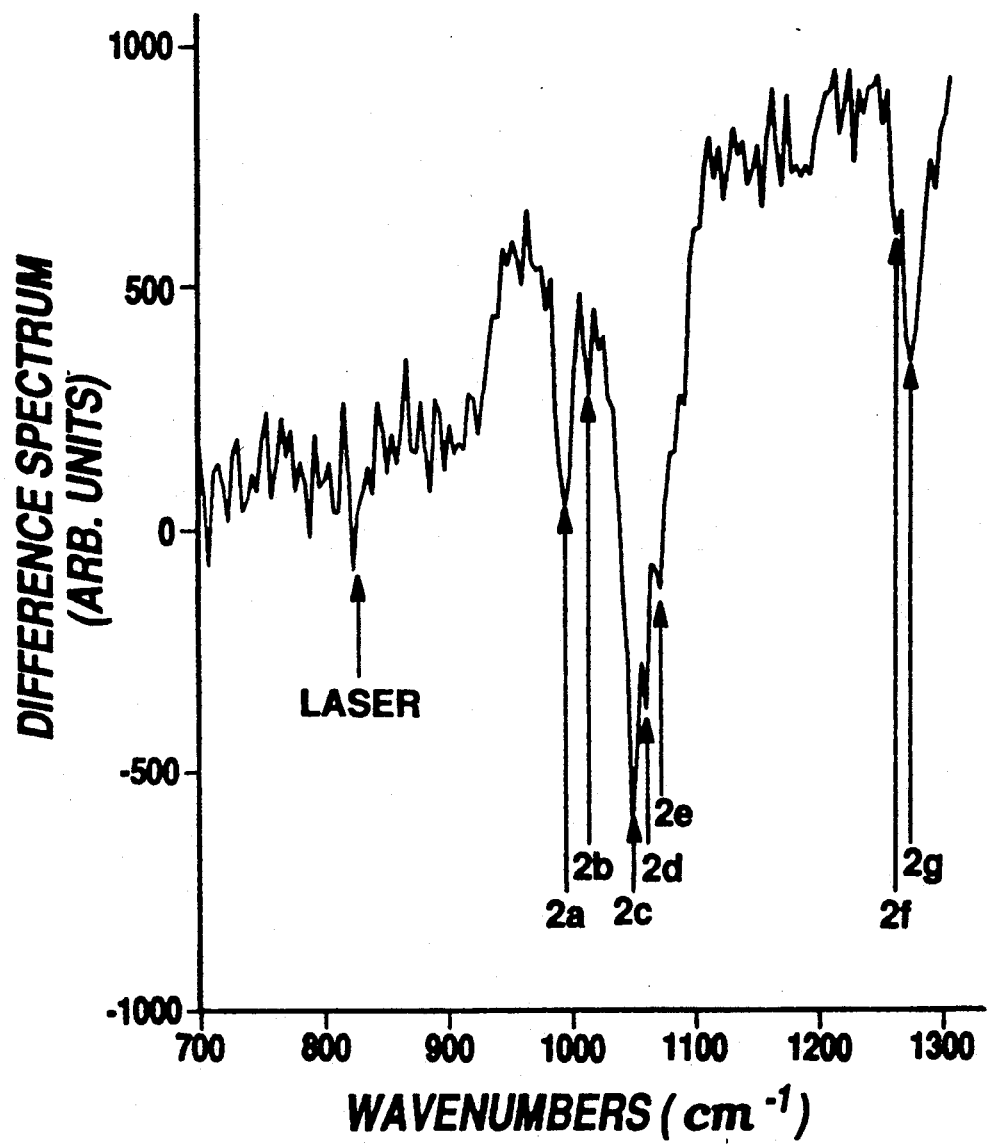
FIG. 3a is a measured different spectrum taken by said photoluminescent sensor from a sand surface contaminated by DMMP and DIMP.
Figure 3B:
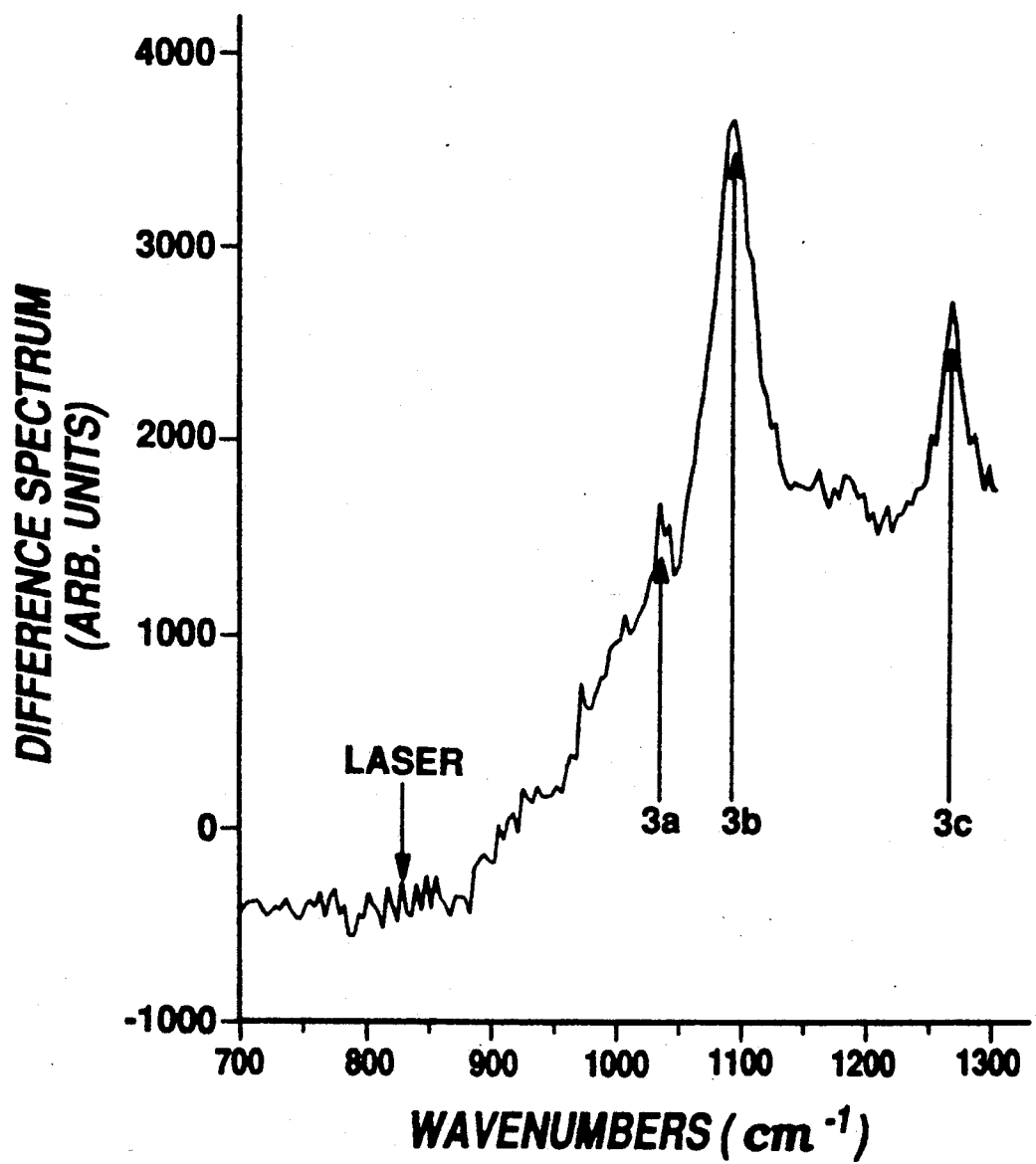
FIG. 3b is a measured difference spectrum taken by said photoluminescence sensor from a soil surface contaminated by SF96.

FIG. 3a and FIG. 3b show plots of contaminated surface data taken with the shutter 13 open, and the photoelastic modulator 17 in either active or non-active operation modes. Data were also recorded and analyzed from contaminated surfaces with the shutter closed (no irradiation). This experiment concluded that surface data recorded and analyzed under ambient conditions have not produced discernible spectral information on all agent simulant contaminants, confirming previous test data taken in the field. In FIG. 3a, a sand surface is wetted by one drop each of DMMP and DIMP contaminants, and in FIG. 3b a soil surface is wetted by one drop of SF96 contaminant. The features labeled as 2a through 2g in FIG. 3A, and as 3a through 3c in FIG. 3B, are explained in the TABLE I hereabove. These labels identify the various contaminant chemicals mentioned in the table, according to the frequency bands specified there that identify a particular chemical.

The difference spectra of FIGS. 3a–b were obtained as follows: (1) the interferometer was calibrated by collecting blackbody radiation 23 passed through the polystyrene calibrator plate, (2) index mirror 19 was placed in position so that detector 41 views the surface and collects a graybody spectrum of said surface, then the shutter 13 is opened, (3) detecting when the surface reaches optimum temperature by detecting a corresponding frequency shift in the graybody spectrum, (4) immediately collecting and rapidly co-adding enough interferograms to assure good signal to-noise ratio, Fourier transform and store, (5) collecting and rapidly co-adding an equal consecutive number of interferograms, Fourier transforming and subtracting same from previous spectra, and (6) matching and discerning a target spectrum.

Referring again to FIG. 3a, the conditions are that one drop each (about one-third millimeter) of DMMP and DIMP contaminants are on a sand sample, and that with an active photoelastic modulator 17, laser intensity 0.63 W cm$^{-2}$, two sets each of 20 interferograms were obtained and were co-added, at 30-34 seconds elapse laser dwell time. Four resonances of DMMP and three resonances of DIMP are evident in the difference spectra data: for DMMP the resonant vibrations are three C-O modes at 1049, 1061, and 1072 cm$^{-1}$ and a P=O mode at 1273 cm$^{-1}$; in DIMP they are two P-O-C stretch modes at 995 and 1014 cm$^{-1}$, and one P=O mode at 1261 cm$^{-1}$ (Table 1).

Vaporization of the simulants via the increasing surface and sub-surface temperature is the primary process responsible for the pronounced spectral detail in the above experimental data. Simulants DMMP and DIMP are considered volatile liquids. In the beginning seconds that the laser irradiates the surface, the simulant vaporization rate rises sharply, causing a vapor cloud to develop with increasing density.

Absorption bands clearly evident in the data of FIG. 3a result from thermal emissions emanating from the sand and transmitting through this vapor cloud. Predominance of DMMP absorption in the difference spectrum of FIG. 3a is attributed in part to its greater volatility, in comparison to that of DIMP, resulting in a larger proportion of its vapor generated by the laser. During irradiation, liquid layers coating the sand surface and sub-surface particles deplete. (Sub-surface evaporation rates are related to the laser beam's penetration depth.) When liquid layers become fully depleted the vapor cloud must dissipate, since its source no longer exits. Calibrating minimum laser dwell time with beam power density for optimum target generation is, therefore, useful for efficient data collection and reduction.

Spectroscopic identification of volatile liquid simulants on rough surfaces via generating a vapor cloud is practical, but it was also proven that the detector can identify non-volatile liquid agent surface contaminants that do not evaporate when irradiated. To demonstrate this capability of the present invention, experiments were performed in which were deposited the above experiments. SF96 is a silicon-based oily liquid. It is non-volatile, and not expected to vaporize in significant concentration when irradiated by the detection system s low intensity (<1 W cm$^{-2}$), 12.1 $\mu$m laser beam. Assignments for this simulant include two Si—O—Si vibrational modes centered at 1034 and 1092 cm$^{-1}$, and a Si—CH$_3$ symmetrical stretching mode at 1265 cm$^{-1}$ (Table 1). A sample of Fourier transformed, subtracted, detector data (steps 1-6, above) is reproduced in FIG. 3b. Laser dwell times is 32-40 seconds for a 0.51 Watt/cm$^2$ intense beam, two sets each of 20 interferograms were co-added, and the photoelectric modulator is active. The ability to detect this non-volatile liquid agent simulant is apparent from the data of FIG. 3b. Bands at 1265 and 1092 cm$^{-1}$ are clearly revealed in the difference spectra, Band the band centered at 1034 cm$^{-1}$ is attenuated.

Absorption bands shown are likely the effect of emissive radiance emanating from the heated soil coating those particles ($T_{soil} > T_{SF96}$). Attenuation of the Si—O—Si band at 1034 cm$^{-1}$ is a result of the transmission properties of filter 31, beam splitter 33, and compensating plate 39. Filter 31, in particular, attenuates nearly 99% energy at 800 cm$^{-1}$, 50% at 1023 cm$^{-1}$, and about 17% at 1094 cm$^{-1}$.

In summary, short range detection of three simulants of chemical agent dispersed on natural sand and soil surfaces were experimentally verified by heating in situ the contaminant, the surface and the subsurfaces with 12.1 $\mu$m IR laser radiation. Nearly 140 Mbytes of data were collected proving that the experimental technique is repeatable and feasible.

It is also possible to replace low pass optical filter 31 with a narrow band laser line rejection filter. Another optional embodiment would be incorporating newer IR interferometer technologies that have orders of magnitude, higher data acquisition rate, such as a solid-state interferometer based on photoelastic modulation technology; replacing IR laser 11 with a maser, beam expanding optics 15 and photoelastic modulator 17 with microwave optics. Mirror 19 may be replaced with one totally reflective at the microwave and the 8-12 $\mu$m IR wavelength bands. It may also be possible to delete filter 31 from the system.

Figure 5A:
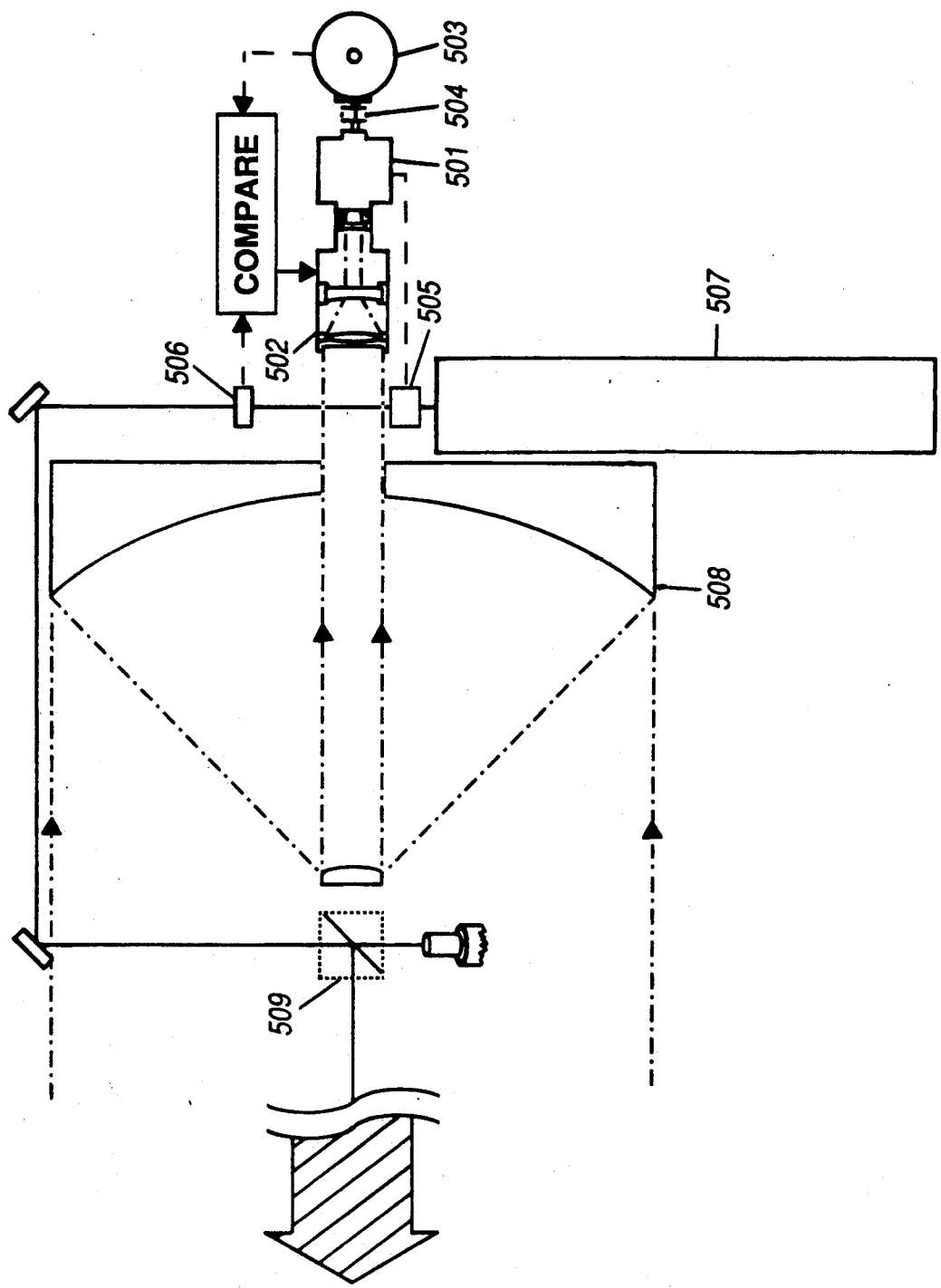
FIGS. 5a–b are a preferred embodiment of the present invention.
Figure 5B:
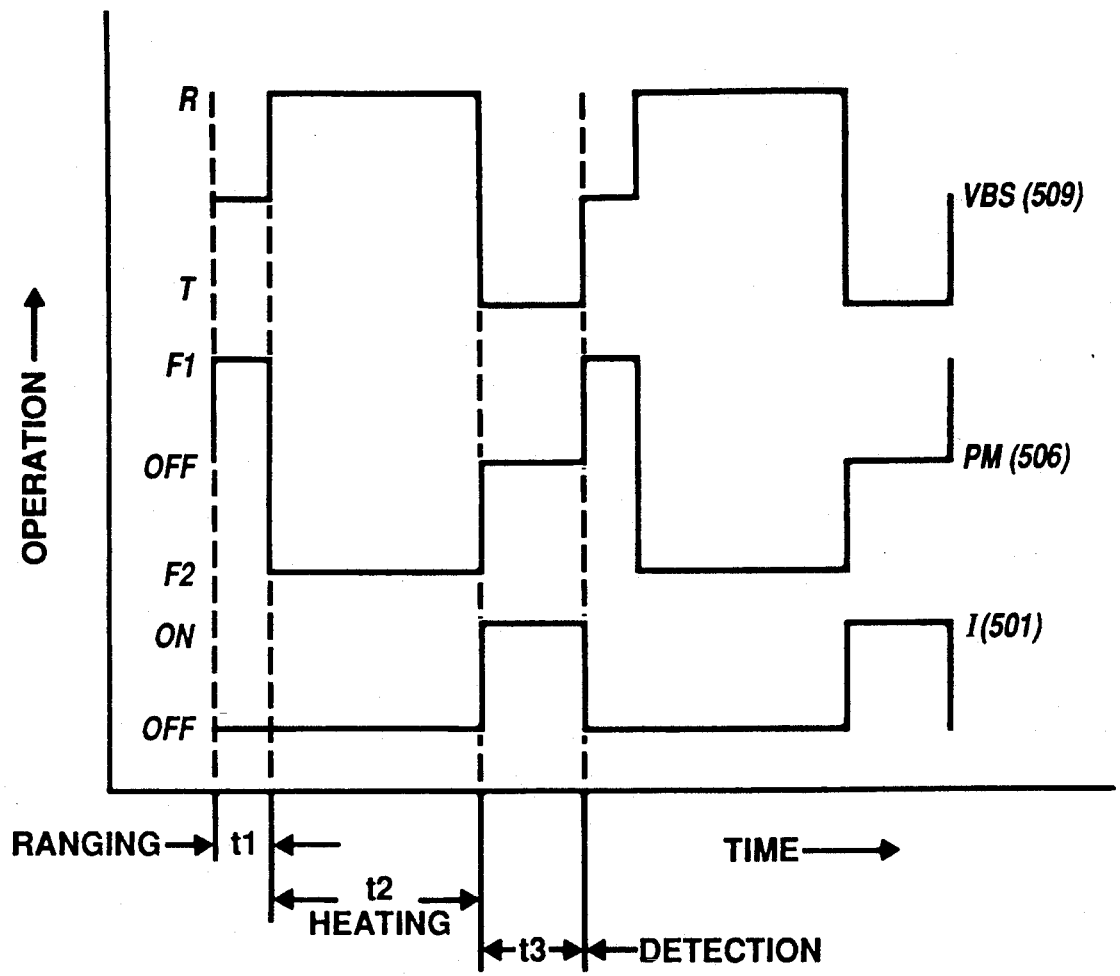

One such embodiment is shown in FIG. 5a. This prototype field photoluminescent sensor consists of a powerful 50 Watt CO$_2$ laser 507 operating at its 'hot' 10P20, 10.6 $\mu$m emission line. The laser beam first transmits through a polarization modulator 506 that operates in two frequency modes: (1) one frequency for efficient photoluminescent production from the heated sample, and (2) the other, much higher frequency, for ranging of the irradiated surface area. Shutter 505 is open during heating and ranging operations and closed during photoluminescent data collection periods by the interferometer 501. A dashed line is shown in FIG. 5A from shutter 505 to interferometer 501 to symbolically indicate the need for these items to have an electrical connection to alternate their operations synchronously. However, the exact electrical circuit is not shown here, but is considered conventional. The variable beamsplitter device 509 adjusts the beam reflectance (transmittance) via an electro-optic circuit in conventional manner (not shown). It is totally transmissive during a photoluminescent data acquisition cycle, totally reflective during the surface heating cycle, and partially reflective during the range finding cycle. A cassegrain telescope 508 collects scattered beam/photoluminescent radiance from the irradiated surface area, passes it through a telephoto lens 502, through the interferometer 501, then the irradiated area is imaged onto the liquid-cooled MCT detector chip 503. The interferometer operates only during photoluminescent collection periods (505 closed) and polarizer 504 is inserted only during ranging periods. During ranging periods, the electronic waveform driving polarization modulator 506 is compared to the scattered-light sinusoid waveform recorded by detector 503. The comparison is made by a skilled operator using conventional equipment and methods (not shown). The comparison operation is merely shown symbolically here. The shift in phase between waveforms (at zero-point crossings in waveform recorded by 503) is a measure of the time-of-flight of the laser beam from source 507 to target surface to detector 503. This information is used to adjust the telephoto lens 502 so that the irradiated cross-section are on the target surface is precisely imaged onto the surface area of the detector chip 503. A typical set of electrical pulses that control sequential operations of variable beamsplitter 509, polarization modulator 506, and interferometer 501 components of this detector embodiment is shown symbolically in FIG. 5b the exact circuitry, which is considered conventional, is not show. However the importance of this diagram is to illustrate that many of the devices in FIG. 5A must alternate their operations, in sequence.

While particular embodiments of the present invention have been illustrated and described herein, it is not intended to limit the invention. It is expected that changes and modifications may be made within the scope of the invention, which is claimed in the following claims.

I claim:

1. A device for remotely detecting any of DMMP, DIMP, or SF96 chemical agent simulants on a remote sand or soil substrate, said device comprising:

infrared projecting means for alternately remotely heating said substrate containing chemical agent simulants comprising a carbon dioxide laser beam, said infrared projecting means comprising a carbon dioxide laser;

photoluminescence sensing means for remotely detecting energy emitted from said substrate, and chemical agent simulants thereon, in response to the infrared heating by said projecting means, said sensing means not operable during the alternating times when said projecting means heats said substrate containing chemical agent simulants; and spectral analyzing means connected to said sensing means and said projecting means for determining the absorption/emission frequency spectral components of detected energy emitted by said substrate and chemical agent simulants thereon and, through comparison with known spectra of the said DMMP, DIMP, and SF96 chemical agent simulants determining the presence of any of said stimulants.

2. The device of claim 1 which further includes a shutter means to alternately block the laser beam from being projected.

3. The device of claim 2 wherein said sensing means operates only when said shutter means is closed to block said laser beam projection.

* * * * *